(12) United States Patent
Schulz et al.

(10) Patent No.: US 7,254,434 B2
(45) Date of Patent: Aug. 7, 2007

(54) VARIABLE PRESSURE REUSABLE SENSOR

(75) Inventors: Christian Schulz, Rancho Santa Margarita, CA (US); Ammar Al-Ali, Tustin, CA (US); Eugene Mason, La Mirada, CA (US)

(73) Assignee: Masimo Corporation, Irvine, CA (US)

( * ) Notice: Subject to any disclaimer, the term of this patent is extended or adjusted under 35 U.S.C. 154(b) by 276 days.

(21) Appl. No.: 10/965,394

(22) Filed: Oct. 13, 2004

(65) Prior Publication Data

US 2005/0085704 A1  Apr. 21, 2005

Related U.S. Application Data

(60) Provisional application No. 60/510,879, filed on Oct. 14, 2003.

(51) Int. Cl.
*A61B 5/00* (2006.01)
(52) U.S. Cl. ........................ 600/344; 600/323
(58) Field of Classification Search ................ 600/309, 600/310, 322, 323, 344
See application file for complete search history.

(56) References Cited

U.S. PATENT DOCUMENTS

| | | | |
|---|---|---|---|
| 4,685,464 A * | 8/1987 | Goldberger et al. ........ 600/344 |
| 4,960,128 A | 10/1990 | Gordon et al. |
| 5,163,438 A | 11/1992 | Gordon et al. |
| 5,337,744 A | 8/1994 | Branigan |
| 5,381,989 A * | 1/1995 | Jackson ................ 248/231.51 |
| 5,431,170 A | 7/1995 | Mathews |
| 5,452,717 A | 9/1995 | Branigan et al. |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,542,421 A * | 8/1996 | Erdman ..................... 600/310 |
| 5,590,649 A | 1/1997 | Caro et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |

(Continued)

*Primary Examiner*—Eric F. Winakur
(74) *Attorney, Agent, or Firm*—Knobbe, Martens, Olson & Bear LLP (57) ABSTRACT

A variable pressure reusable sensor has a first jaw having a first hinge and an emitter and an opposing second jaw having a second hinge and a detector. A pin is disposed through the first and second hinges so as to rotatably attach the first and second jaws. The jaws are adapted to attach to a tissue site so that the emitter transmits optical radiation into the tissue site and the detector receives optical radiation after absorption by the tissue site. A spring having a plurality of legs is disposed around the pin and configured so that the legs apply force to the jaws. A tensioner is disposed proximate at least one of the jaws and configured to variably position at least one of the legs so as to adjust pressure exerted by the jaws on the tissue site.

15 Claims, 7 Drawing Sheets

U.S. PATENT DOCUMENTS

| | | |
|---|---|---|
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,078,828 A * | 6/2000 | Yasuda et al. ............... 600/310 |
| 6,081,735 A | 6/2000 | Diab et al. |
| 6,088,607 A | 7/2000 | Diab et al. |
| 6,110,522 A | 8/2000 | Lepper, Jr. et al. |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,236,872 B1 | 5/2001 | Diab et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,334,065 B1 | 12/2001 | Al-Ali et al. |
| 6,349,228 B1 | 2/2002 | Kiani et al. |
| 6,360,114 B1 | 3/2002 | Diab et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,061 B2 * | 1/2003 | Larson ....................... 600/323 |
| 6,515,273 B2 | 2/2003 | Al-Ali |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,711,789 B2 * | 3/2004 | Ping ........................... 24/505 |
| 6,714,804 B2 | 3/2004 | Al-Ali et al. |
| RE38,492 E | 4/2004 | Diab et al. |
| 6,725,075 B2 | 4/2004 | Al-Ali |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,983,178 B2 * | 1/2006 | Fine et al. .................. 600/335 |

* cited by examiner

VARIABLE PRESSURE REUSABLE SENSOR

REFERENCE TO RELATED APPLICATION

The present application claims priority benefit under 35 U.S.C. §119(e) from U.S. Provisional Application No. 60/510,879, filed Oct. 14, 2003, entitled "VARIABLE PRESSURE REUSABLE SENSOR," which are incorporated herein by reference.

BACKGROUND OF THE INVENTION

Pulse oximeters perform a spectral analysis of the pulsatile component of arterial blood in order to determine oxygen saturation, the relative concentration of oxygenated hemoglobin to depleted hemoglobin. Pulse oximeters have gained rapid acceptance in a wide variety of medical applications, including surgical wards, intensive care units, general wards and home care by providing early detection of decreases in the arterial oxygen supply, reducing the risk of accidental death and injury. A pulse oximetry system consists of a sensor, a monitor and a patient cable providing electrical communication between the sensor and monitor. The sensor attaches to a patient tissue site and provides a physiological signal to the monitor, which continuously displays patient oxygen saturation and pulse rate measurements.

A pulse oximetry sensor has emitters typically consisting of a red light emitting diode (LED) and an infrared LED that project light through blood vessels and capillaries underneath a tissue site, such as a fingernail bed. The sensor also has a detector typically consisting of a photodiode positioned opposite the LEDs so as to detect the emitted light as it emerges from the tissue site. Sensor types include a disposable sensor and a reusable sensor. A disposable sensor attaches to a patient tissue site with an adhesive wrap and is intended for use by only a single patient. A reusable sensor clips onto a patient tissue site and is intended for repeated use on multiple patients.

Figure 1:
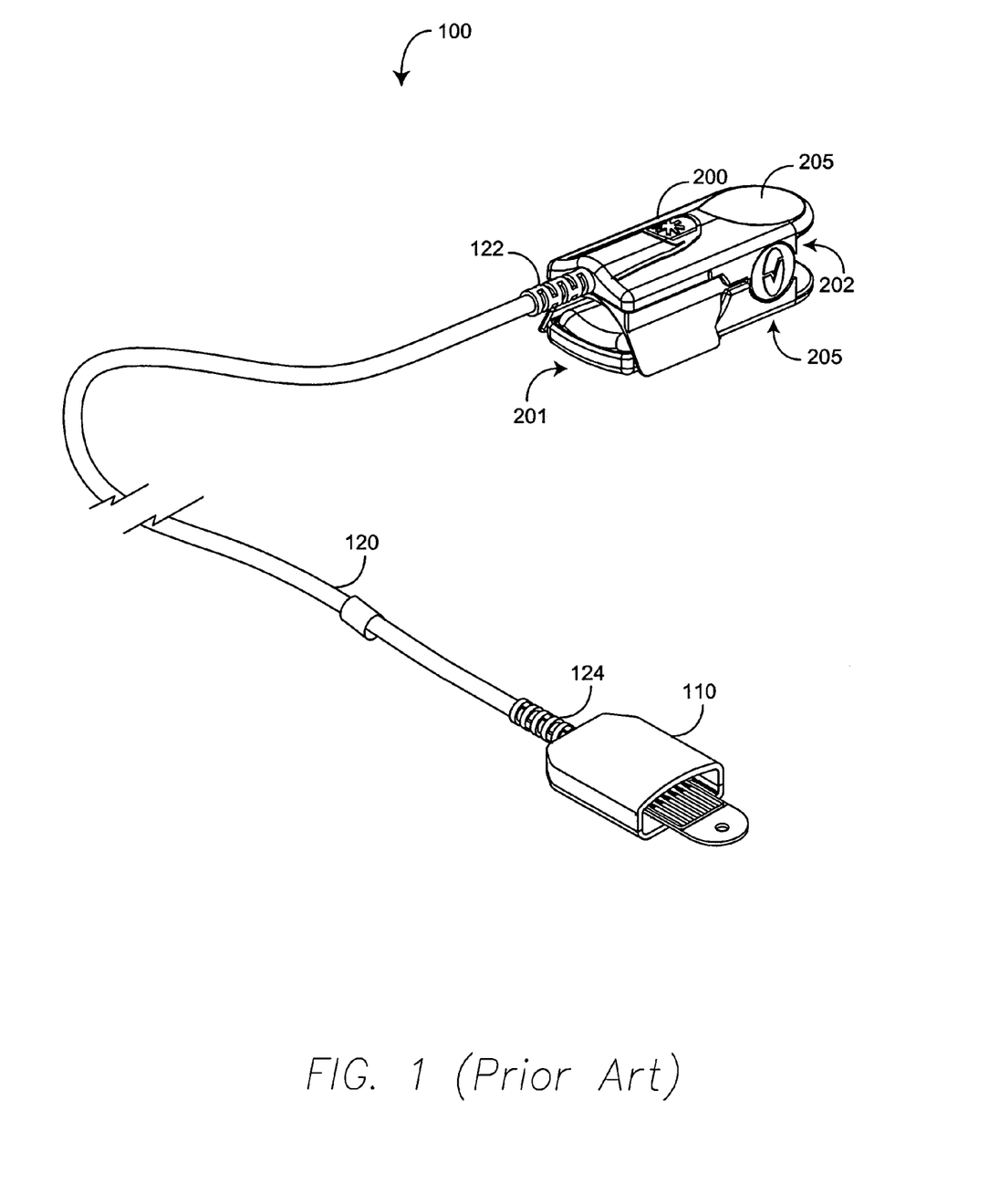
FIGS. 1-2 are assembled and exploded perspective views, respectively, of a prior art reusable finger sensor.

FIG. 1 illustrates a reusable finger sensor 100 having a sensor clip 200, a sensor connector 110 and a sensor cable 120. The sensor clip 200 has an open position for inserting a finger, typically the index finger, and a close position (shown) for securing the sensor clip 200 to opposite sides of the finger. The clip 200 has a front end 201 and a back end 202. A finger is inserted into the front end 201 in the open position. The clip 200 is moved between the close position and the open position by pressing on and releasing the finger grips 205 at the back end 202. A spring 280 (FIG. 2) applies force to the back end 202 that determines the pressure on an inserted finger in the closed position. The sensor clip 200 is described in further detail with respect to FIG. 2, below.

Also shown in FIG. 1, the sensor connector 110 plugs into a patient cable (not shown). The sensor cable 120 has a first end 122 terminating at the sensor clip 200 and a second end 124 terminating at the sensor connector 130. The sensor cable 120 electrically communicates monitor originated LED drive signals from the connector 110 to the sensor clip 200 and monitor destined detector signals from the sensor clip 200 to the connector 110.

Figure 2:
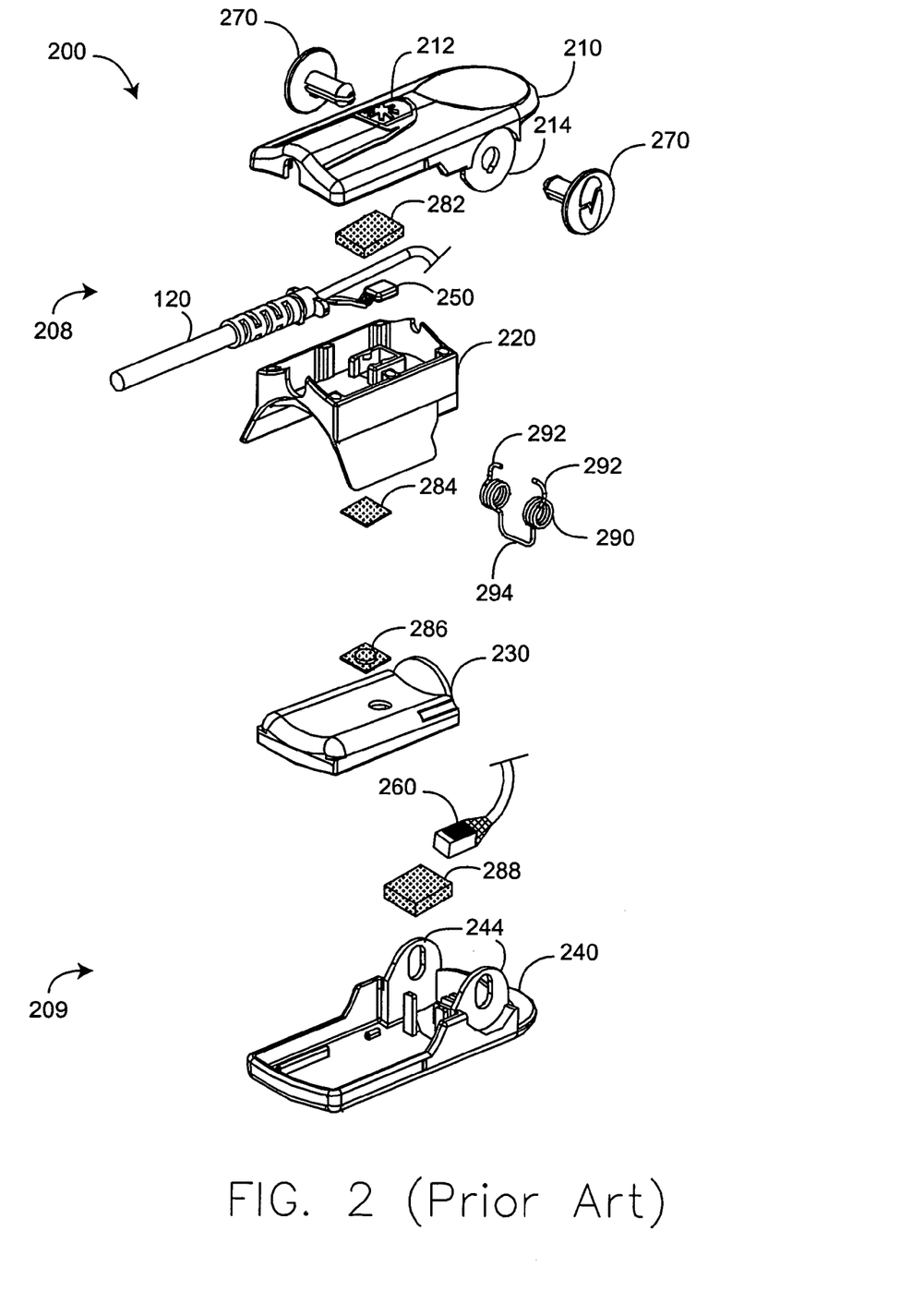

FIG. 2 further illustrates a reusable sensor clip 200 having a top shell 210, a top pad 220, a bottom pad 230, a bottom shell 240, an emitter 250, a detector 260, hinge pins 270 and a spring 290. The top shell 210 and top pad 220 retain the cable 120 and emitter 250 to form a top jaw 208. The bottom shell 240 and bottom pad 230 retain the detector 260 to form a bottom jaw 209. The clip 200 is assembled with the hinge pins 270 inserted through hinges 214, 244 and the spring 290 so as to rotatably attach the jaws 208, 209 and retain the spring between the jaws 208, 209. The spring 290 has legs 292 that apply force to the top shell 210 and a center section 294 that applies tension to the bottom shell 240, urging the jaws 208, 209 to a closed position in which the pads 220, 230 are held against a tissue site. Pressure sensitive adhesive (PSA) 282, 288 adheres the emitter 250 to the top shell 210 and the detector 260 to the bottom shell 240. Windows 284, 286 pass light from the emitter 250 to the detector 260. A finger is inserted into the clip 200 in an orientation shown on the top shell 210.

SUMMARY OF THE INVENTION

A conventional reusable sensor has a fixed pressure, that is, it applies a predetermined force to a tissue site at a particular jaw position that depends on the characteristics of a spring. A fixed pressure sensor poses several problems. Sensor pressure set at time of manufacture cannot easily accommodate variations in tissue sites, patient ages or sizes, sensitivities to pressure, and perfusion characteristics. Excess pressure restricts blood flow in the tissue site and is uncomfortable for the patient. Insufficient pressure fails to keep the sensor attached to a particular tissue site. Further, a pulse oximetry sensor may be used in applications not foreseen by the manufacturer, such as attachment to unconventional tissue sites or use on animals.

One aspect of a variable pressure reusable sensor is a clip having a first jaw with a first hinge and an emitter and an opposing second jaw with a second hinge and a detector. A pin is disposed through the first and second hinges so as to rotatably attach the first and second jaws. The jaws are adapted to attach to a tissue site so that the emitter transmits optical radiation into the tissue site and the detector receives optical radiation after absorption by the tissue site. A spring having a plurality of legs is disposed around the pin and configured so that the legs apply force to the jaws. A tensioner is disposed proximate at least one of the jaws and configured to variably position at least one of the legs so as to adjust pressure exerted by the jaws on the tissue site.

Another aspect of a variable pressure reusable sensor comprises providing a sensor clip having an open position for inserting and removing a tissue site and a closed position for attaching the clip to the tissue site. Optical radiation is emitted into the tissue site in the closed position and received after absorption by the tissue site. A physiological signal is generated that is responsive to the absorption. The clip is urged to the closed position with a variable force so as to adjust the pressure of the clip against the tissue site.

A further aspect of a variable pressure reusable sensor comprises a plurality of jaws adapted to attach to a tissue site. The jaws have an emitter that transmits optical radiation into the tissue site and a detector that receives optical radiation after absorption by the tissue site. A selected spring configuration is disposed proximate the jaws so as to apply force to the jaws. A spring set provides a range of tension characteristics. The selected spring configuration is chosen from the spring set so as to provide a particular pressure profile on the tissue site.

DETAILED DESCRIPTION OF THE PREFERRED EMBODIMENT

Figure 3A:
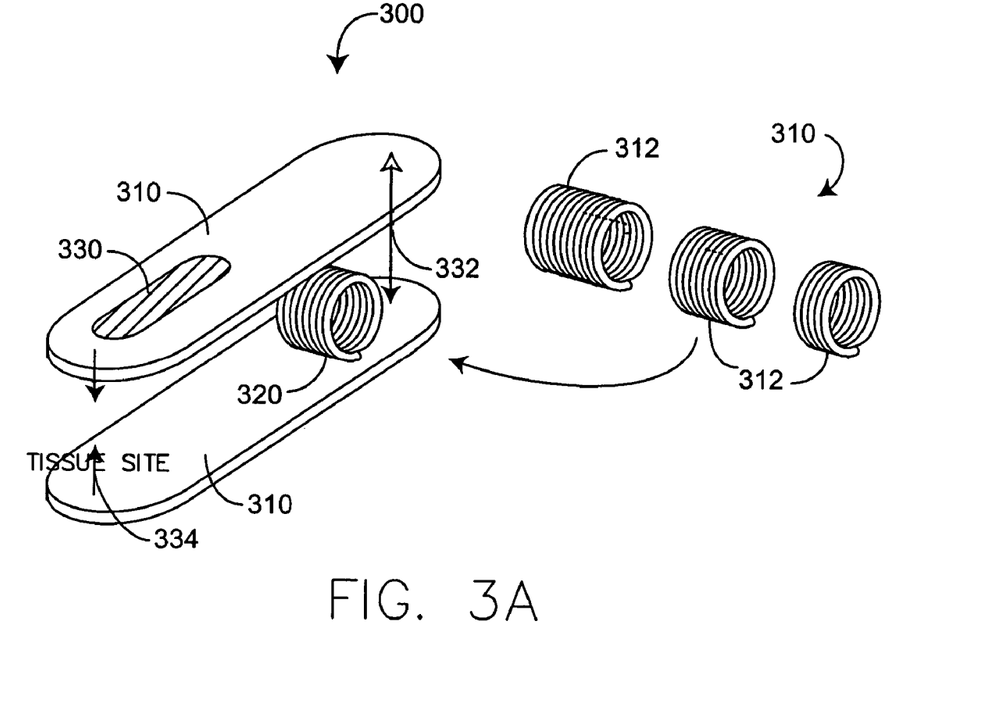
FIG. 3A-B are perspective depictions of a variable pressure sensor clip having a selectable spring set and an adjustable tension spring, respectively.
Figure 3B:
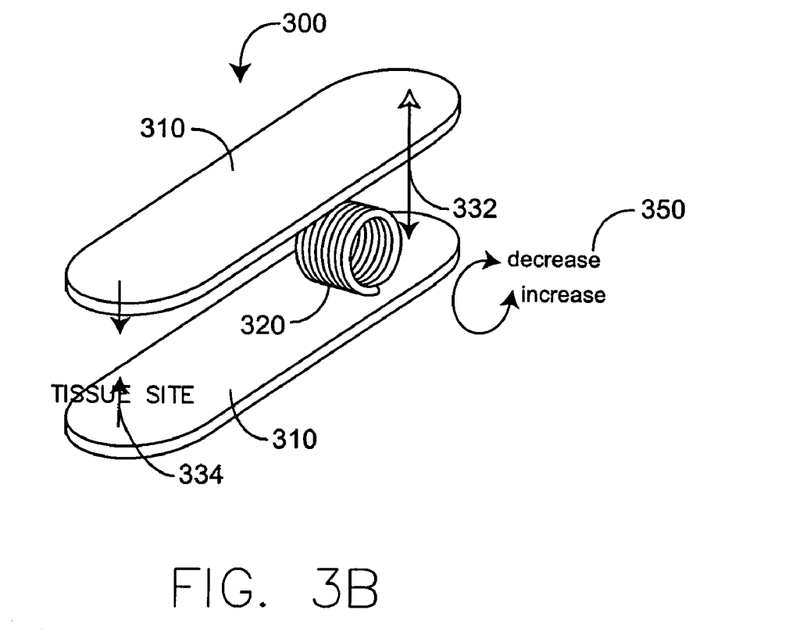
Figure 4A:
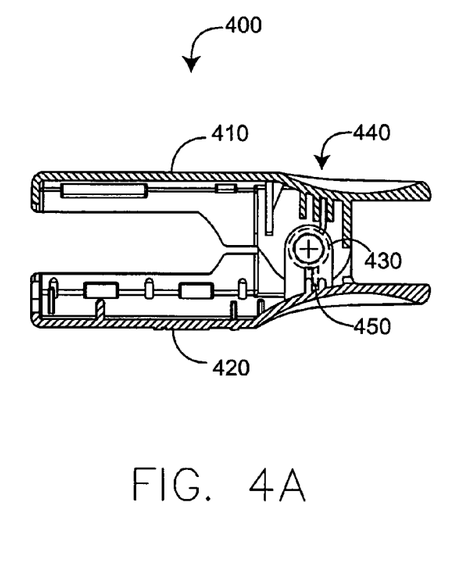
FIGS. 4A-D are a cross-sectional side view, an upper jaw cross-sectional side view, a lower jaw top view, and an upper jaw bottom view, respectively, of a variable pressure sensor clip having multiple tension-selection slots.
Figure 4B:
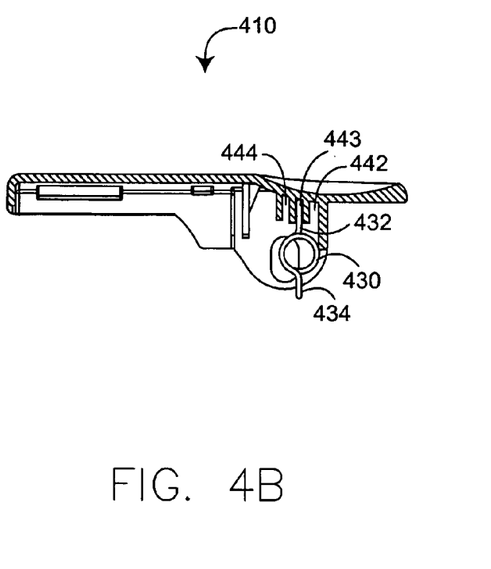
Figure 4C:
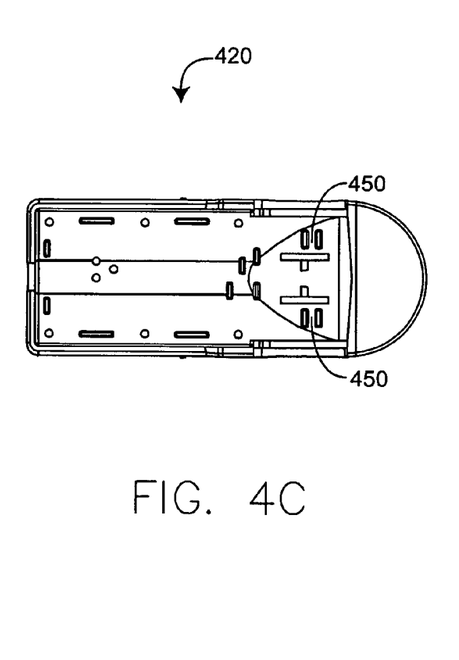
Figure 4D:
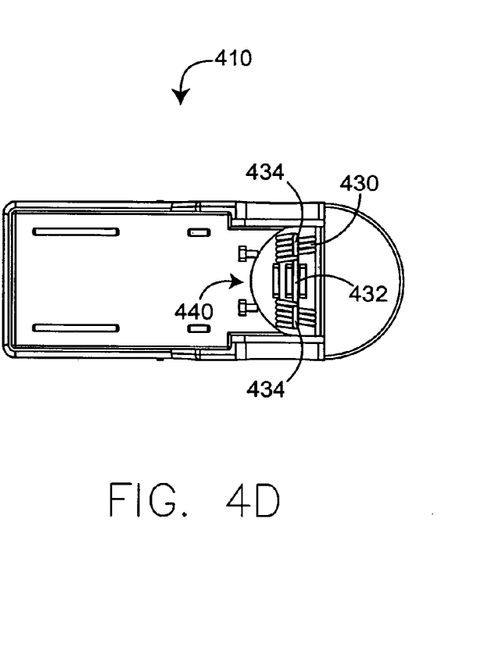

FIGS. 3A-B generally illustrate a variable pressure sensor clip 300 for a reusable sensor having opposing jaws 310 configured to clamp onto a tissue site placed between the jaws 310 with a pressure determined by a corresponding spring 320. For example, the jaws 310 may be pivotably connected by a hinge, with the spring 320 applying a spring force 332 on one section of the jaws 310 that is translated to a pressure 334 applied to the tissue site. The spring force 332 is determined by the tension characteristics of the spring 320, which is selectable when the sensor is manufactured, as described with respect to FIG. 3A, or adjustable, as described with respect to FIG. 3B.

As shown in FIG. 3A, one embodiment of the variable pressure sensor clip 300 utilizes a spring set 310 having various spring types 312. The spring 320 incorporated into a particular sensor 300 is a selected one of the spring types 312. Each spring type 312 is designed with different tension characteristics, so as to provide a preselected pressure profile on a tissue site, such as pressure versus tissue site thickness. The pressure profile for each spring type 312 is derived from a unique combination of spring material, leg configuration, coil radius, number of coils, and coil thickness, within the constraints of a particular sensor configuration. An encoded label 330, or other visual indication of the selected spring type 312 is applied to the sensor 300 advantageously allowing a health care provider or other user to easily identify a desired sensor for a particular situation. In a particular embodiment, the label 330 is color coded and fixedly attached on one or both of the jaws 320. For example, a red label may correspond to a heavy pressure sensor, a green label to a moderate pressure sensor, and a blue label to a light pressure sensor. Alternatively, the clip 300 is at least partially made of a colored material corresponding to sensor pressure. During manufacture, the spring 320 is chosen from the spring set 310, the spring 320 is assembled into the sensor 330, and the encoded label 330 is applied according to the selected spring type 312. In an alternative embodiment, sensor pressure is determined by the number of springs incorporated into the clip 300.

As shown in FIG. 3B, another embodiment of the variable pressure reusable sensor 300 utilizes an adjustable tensioner 350, which increases or decreases the tension in the spring 320 by controlling the position of one or more of the spring legs. For example, a spring leg can be moved in the same direction as the spring coils so as to increase the spring tension, increasing the pressure on the tissue site. A spring leg can be moved in the opposite direction as the spring coils so as to decrease the spring tension and decrease the pressure on the tissue site. In one embodiment, the tensioner 350 has multiple tension-selection slots, as described with respect to FIGS. 4A-D, below. In another embodiment, the tensioner 350 is a movable spring-leg retaining wall, as described with respect to FIGS. 5A-B, below. In yet another embodiment, the tensioner 350 is a movable spring-leg supporting wedge, as described with respect to FIGS. 6A-C, below FIGS. 4A-D illustrate a slot tensioner clip 400, which advantageously provides a variable pressure by positioning a spring leg in one of multiple spaced slots during sensor assembly. Thus, a particular sensor pressure is selected at the time of manufacture, and a color coded label or other visible encoding of the selected pressure can be applied accordingly, in a manner similar to that described with respect to FIG. 3A, above. The clip 400 has an upper jaw 410, an opposing lower jaw 420, a spring 430, multiple tension slots 440 disposed on the upper jaw 410 and a fixed slot 450 disposed on the lower jaw 420. The spring 430 has a center leg 432 and two end legs 434. The two end legs 434 are assembled into the fixed slot 450, and the center leg 432 is selectively assembled into one of the tension slots 440 according to the desired pressure characteristics for a particular sensor. In one embodiment, three tension slots 442, 443, 444 are formed from three spaced walls extending perpendicularly underneath the finger-grip portion of the upper jaw 410 and partially extending parallel to the axis of the spring 430. A first slot 442 precoils the spring 430 the most and results in the greatest tissue pressure. A second slot 443, shown capturing the center leg 432, results in a moderate tissue pressure. A third slot 444 precoils the spring 430 the least and results in the lowest tissue pressure.

Figure 5A:
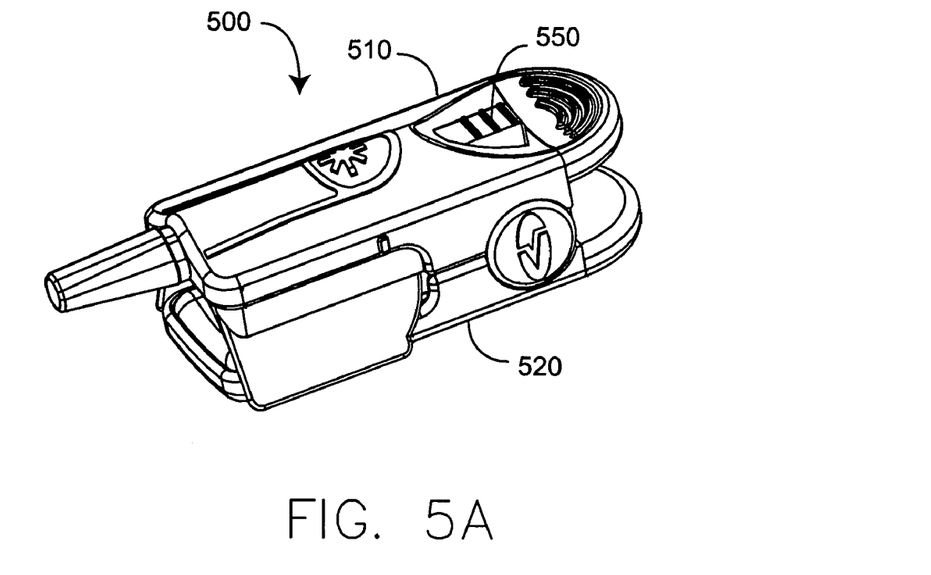
FIGS. 5A-B are perspective and upper jaw bottom views, respectively, of a variable pressure sensor clip having a movable spring-leg retaining wall.
Figure 5B:
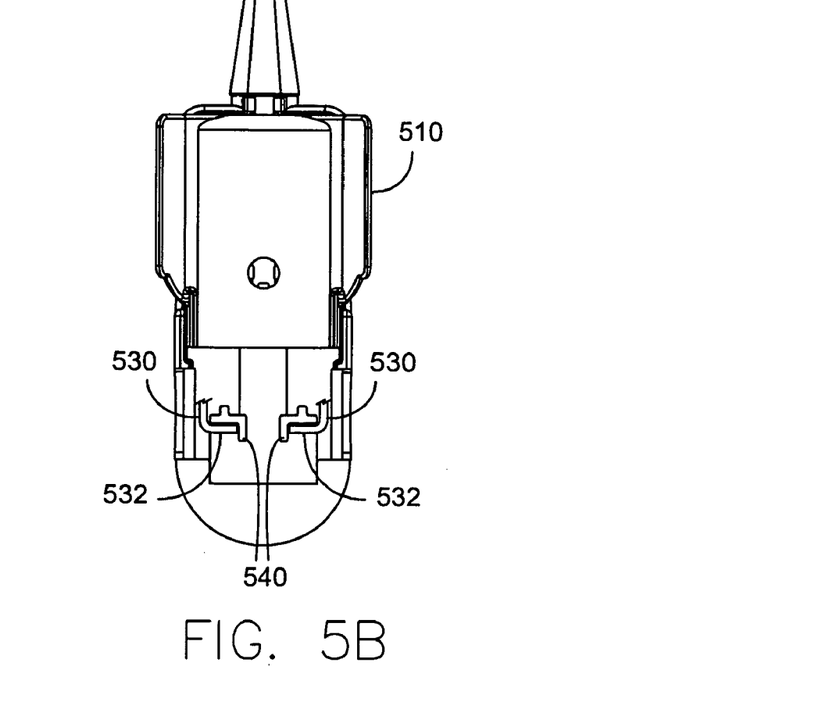

FIGS. 5A-B illustrate a wall tensioner clip 500, which provides a variable pressure by retaining a spring leg with a movable wall. Thus, sensor pressure can be advantageously adjusted by a sensor user. The clip 500 has an upper jaw 510, an opposing lower jaw 520, a spring 530 having spring legs 532, a retaining wall 540 and a thumb switch 550. The retaining wall 540 holds the spring legs 532, is slidably retained by the upper jaw 510 and is in mechanical communications with the thumb switch 550. The thumb switch 550 extends through a slot in the upper jaw 510 and can be positioned backward and forward so as to slide the retaining wall back and forth and, correspondingly, move the spring legs 532. In this manner, precoil in the spring 530 can be increased or decreased, adjusting sensor pressure on a tissue site. In one embodiment, the thumb switch 550 is a spring-loaded push button that lifts a ratcheted lever from corresponding teeth so as to release the retaining wall. In another embodiment, the thumb switch 550 is replaced by a set screw retained and recessed into the upper jaw 510. The set screw engages a threaded wall that extends into the upper jaw 510 from the retaining wall 540 so as to actuate the retaining wall 540 as the set screw is turned. In this manner, the sensor pressure is easily adjusted after manufacture but inadvertent modification of sensor pressure is unlikely.

Figure 6A:
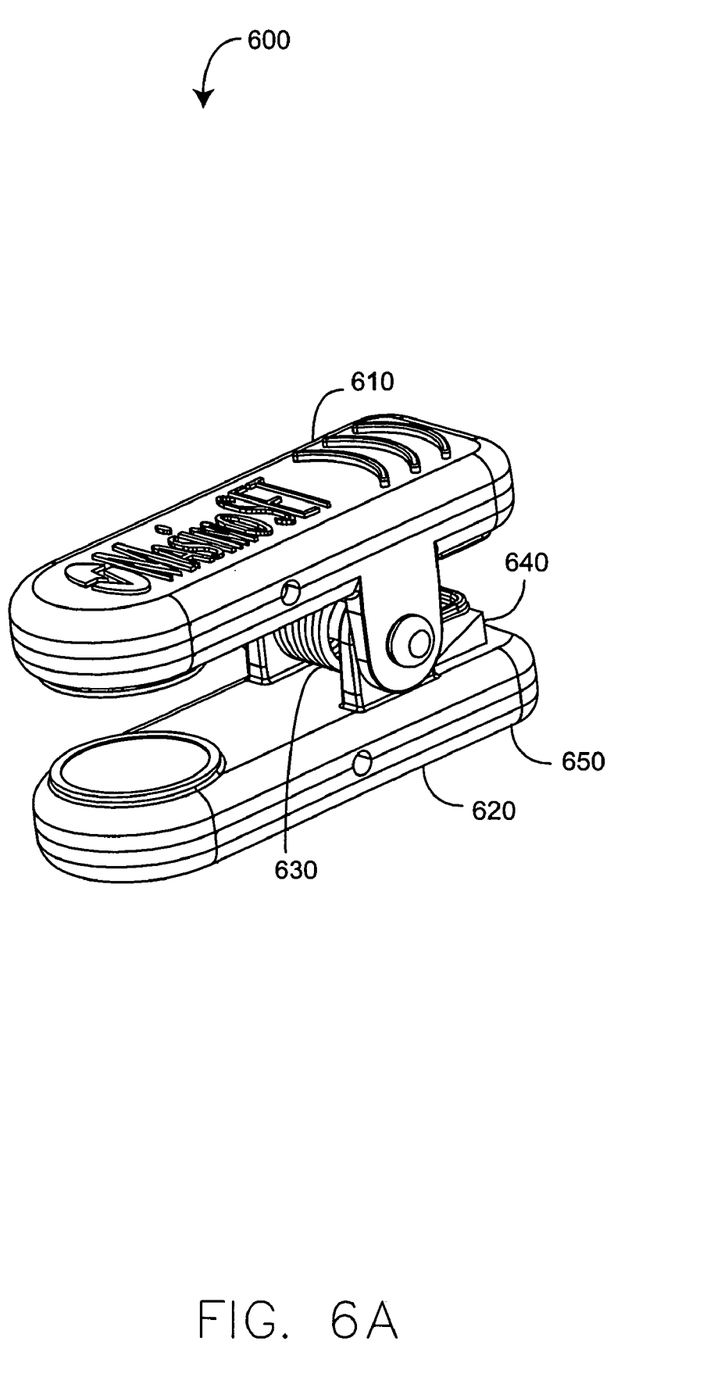
FIGS. 6A-C are perspective, side, and cutaway views, respectively, of a variable pressure sensor clip having a movable spring-leg supporting wedge.
Figure 6B:
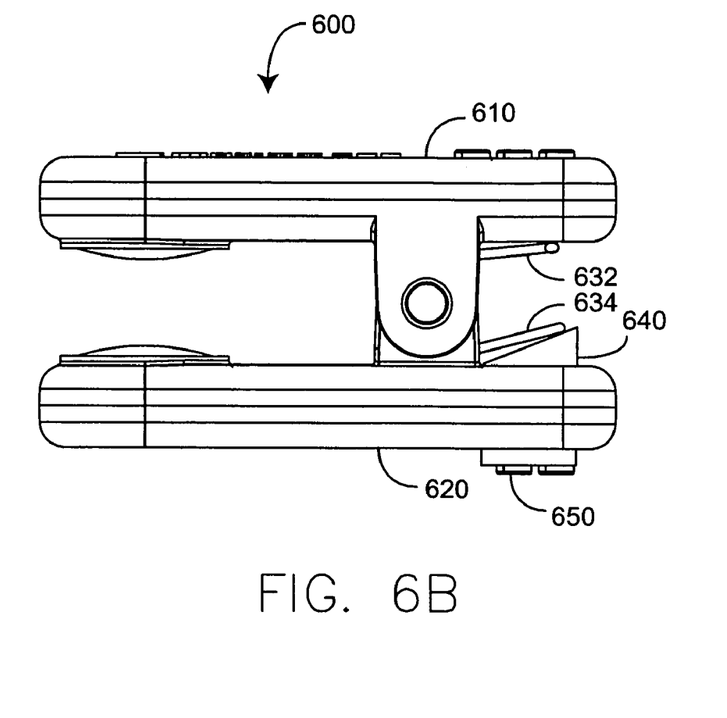
Figure 6C:
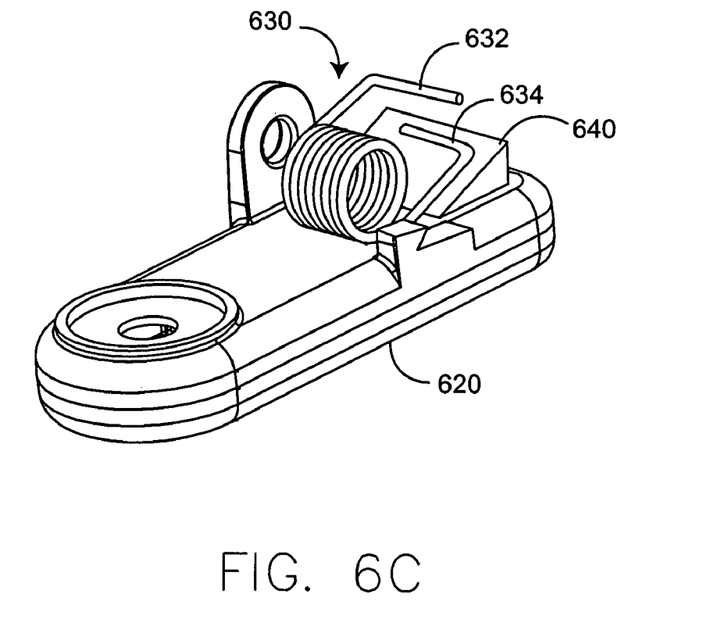

FIGS. 6A-C illustrate a wedge tensioner clip 600, which provides a variable pressure by positioning a spring leg with a movable wedge. As with the wall tensioner clip 500 (FIGS. 5A-B), sensor pressure can be advantageously adjusted by a sensor user. The clip 600 has an upper jaw 610, an opposing lower jaw 620, a spring 630 having spring legs 632, 634, a wedge 640 and a thumb switch 650. An upper spring leg 632 is supported against the upper jaw 610 and a lower spring leg 634 is supported against the wedge 640. The wedge 640 is slidably retained by the lower jaw 610 and is in mechanical communications with the thumb switch 650. The thumb switch 650 extends through a slot in the lower jaw 620 and can be positioned backward and forward so as to slide the wedge back and forth and, correspondingly, lower and raise the lower spring leg 634. In this manner, precoil in the spring 630 can be increased or decreased, adjusting the sensor pressure on a tissue site.

In one embodiment, the thumb switch 650 is a spring-loaded push button that lifts a ratcheted lever from corresponding teeth so as to release the wedge 640. In another embodiment, the thumb switch 650 is replaced by a set screw retained and recessed into the lower jaw 620. The set screw engages a threaded wall that extends into the lower jaw 620 from the wedge 640 so as to actuate the wedge 640 as the set screw is turned.

A variable pressure reusable sensor has been disclosed in detail in connection with various embodiments. These embodiments are disclosed by way of examples only and are not to limit the scope of the claims that follow. One of ordinary skill in art will appreciate many variations and modifications.

What is claimed is:

1. A variable pressure noninvasive pulse oximeter reusable sensor comprising:
   a first jaw having a first hinge and an emitter;
   an opposing second jaw having a second hinge and a detector;
   a pin disposed through said first and second hinges so as to rotatably attach said first and second jaws to form a sensor clip;
   said jaws adapted to attach to a tissue site so that said emitter transmits optical radiation into said tissue site and said detector receives said optical radiation after absorption by said tissue site;
   a spring having a plurality of legs, said spring disposed around said pin and configured so that said legs apply force to said jaws; and
   a tensioner disposed proximate at least one of said jaws and configured to cause said spring to exert variable pressure through said jaws on said tissue site responsive to varying tensioner positions or configurations with respect to said spring.

2. The reusable sensor according to claim 1 wherein said tensioner comprises plurality of slots each configured to hold at least one of said legs in a corresponding one of a plurality of leg positions that determine the tension in said spring.

3. The reusable sensor according to claim 2 wherein:
   said slots are disposed on said first jaw, said spring has a center leg and two end legs, said center leg is positioned in one of said slots, and said end legs are positioned against said second jaw.

4. The reusable sensor according to claim 1 wherein said tensioner comprises slidable wall configured to retain at least one of said legs, said wall movable to a plurality of leg positions that determine the tension in said spring.

5. The reusable sensor according to claim 1 wherein said tensioner comprises wedge configured to support at least one of said legs, said wedge movable to a plurality of leg positions that determine the tension in said spring.

6. The reusable sensor according to claim 1 further comprising a screw retained by one of said jaws, said screw in mechanical communications with said tensioner so as to adjust said tensioner as said screw is turned.

7. The reusable sensor according to claim 1 further comprising a thumb switch retained by and protruding from one of said jaws, said thumb switch adapted to release and adjust said tensioner.

8. A method of attaching a variable pressure noninvasive pulse oximetry reusable sensor to a tissue site of a patient, the method comprising the steps of:
   providing a noninvasive pulse oximetry sensor clip having an open position for inserting and removing a tissue site and a closed position for attaching said clip to said tissue site;
   adjusting the force exerted against said tissue site to a desired level;
   urging said clip to said closed position against said tissue site at said desired level of force.

9. The variable tension reusable sensor method according to claim 8 wherein said adjusting of said clip comprises the substeps of:
   selecting a spring from a spring set; and
   incorporating said spring into said clip.

10. The variable tension reusable sensor method according to claim 8 wherein said adjusting of said clip comprises the substeps of:
    selecting a predetermined number of springs of a spring type; and
    incorporating said springs into said clip.

11. The variable tension reusable sensor method according to claim 8 wherein said adjusting of said clip comprises the substep of adjusting a tensioner.

12. The variable tension reusable sensor method according to claim 11 wherein said adjusting substep comprises the substeps of:
    selecting a particular slot from a plurality of slots fixedly attached to a first jaw; and
    placing a spring leg into said particular slot.

13. The variable tension reusable sensor method according to claim 11 wherein said adjusting substep comprises the substeps of:
    capturing a spring leg with a retaining wall; and
    adjusting the position of said wall.

14. The variable tension reusable sensor method according to claim 11 wherein said adjusting substep comprises the substeps of:
    supporting a spring leg with a wedge; and
    adjusting the position of said wedge.

15. The variable tension reusable sensor method according to claim 11 wherein said adjusting substep comprises the substep of pushing a switch on said sensor clip so as to release said tensioner.

* * * * *

UNITED STATES PATENT AND TRADEMARK OFFICE
CERTIFICATE OF CORRECTION

| | | |
|---|---|---|
| PATENT NO. | : 7,254,434 B2 | Page 1 of 1 |
| APPLICATION NO. | : 10/965394 | |
| DATED | : August 7, 2007 | |
| INVENTOR(S) | : Christian Schulz et al. | |

It is certified that error appears in the above-identified patent and that said Letters Patent is hereby corrected as shown below:

On the Title Page Item (75) (Inventors), line 4, delete "Mirada," and insert -- Habra Heights, --, therefor.

At column 5, line 37, in Claim 2, after "comprises" insert -- a --.

At column 5, line 41, in Claim 3, delete "wherein:" and insert -- wherein --, therefor.

At column 5, line 47, in Claim 4, after "comprises" insert -- a --.

At column 5, line 51, in Claim 5, after "comprises" insert -- a --.

At column 6, line 19 (Approx.), in Claim 9, after "adjusting" delete "of".

At column 6, line 25 (Approx.), in Claim 10, after "adjusting" delete "of".

At column 6, line 31, in Claim 11, after "adjusting" delete "of".

Signed and Sealed this

Fourteenth Day of April, 2009

JOHN DOLL
*Acting Director of the United States Patent and Trademark Office*